US00PP23960P2

(12) United States Plant Patent
Misato

(10) Patent No.: US PP23,960 P2
(45) Date of Patent: Oct. 8, 2013

(54) ***MANDEVILLA* PLANT NAMED 'SUNPARASWEPI'**

(50) Latin Name: *Mandevilla hybrida*
Varietal Denomination: Sunparaswepi

(75) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 76 days.

(21) Appl. No.: 13/374,303

(22) Filed: Dec. 20, 2011

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Annette Para
(74) *Attorney, Agent, or Firm* — C. A. Whealy

(57) ABSTRACT

A new and distinct cultivar of *Mandevilla* plant named 'Sunparaswepi', characterized by its compact and vining plant habit; vigorous growth habit; freely branching habit and short internodes, dense and bushy plant form; freely flowering habit; medium-sized pink to white-colored flowers; and long flowering period.

1 Drawing Sheet

Botanical designation: *Mandevilla hybrida.*
Cultivar denomination: 'SUNPARASWEPI'.

BACKGROUND OF THE INVENTION

The present invention relates to a new and distinct cultivar of *Mandevilla* plant, botanically known as *Mandevilla hybrida* and hereinafter referred to by the name 'Sunparaswepi'.

The new *Mandevilla* plant is a product of a planned breeding program conducted by the Inventor in Higashiomi, Shiga, Japan. The objective of the breeding program is to create new freely-branching *Mandevilla* plants with numerous pink to white-colored flowers.

The new *Mandevilla* plant originated from a cross-pollination conducted by the Inventor in Higashiomi, Shiga, Japan in April, 2006 of a proprietary selection of *Mandevilla hybrida* identified as code number M-7, not patented, as the female, or seed parent with a proprietary selection of *Mandevilla hybrida* identified as code number MW-13, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2007.

Asexual reproduction of the new *Mandevilla* plant by cuttings in Higashiomi, Shiga, Japan, since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparaswepi'. These characteristics in combination distinguish 'Sunparaswepi' as a new and distinct *Mandevilla* plant:

1. Compact and vining plant habit.
2. Vigorous growth habit.
3. Freely branching habit and short internodes, dense and bushy plant form.
4. Freely flowering habit.
5. Medium-sized pink to white-colored flowers.
6. Long flowering period.

Plants of the new *Mandevilla* can be compared to plants of the female parent selection. Plants of the new *Mandevilla* differ primarily from plants of the female parent selection in the following characteristics:

1. Plants of the new *Mandevilla* have smaller leaves than plants of the female parent selection.
2. Plants of the new *Mandevilla* have smaller flowers than plants of the female parent selection.
3. Plants of the new *Mandevilla* and the female parent selection differ in flower color as plants of the female parent selection have white-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* have larger leaves than plants of the male parent selection.
2. Plants of the new *Mandevilla* have larger flowers than plants of the male parent selection.
3. Plants of the new *Mandevilla* and the male parent selection differ in flower color as plants of the male parent selection have light pink-colored flowers.

Plants of the new *Mandevilla* can be compared to plants of the *Mandevilla* 'Sunparamiho', disclosed in a U.S. Plant patent application Ser. No. 12/804,921. In side-by-side comparisons conducted in Higashiomi, Shiga, Japan, plants of the new *Mandevilla* differed from plants of 'Sunparamiho' in the following characteristics:

1. Plants of the new *Mandevilla* had shorter internodes than plants of 'Sunparamiho'.

2. Plants of the new *Mandevilla* had smaller leaves than plants of 'Sunparamiho'.
3. Plants of the new *Mandevilla* and 'Sunparamiho' differed in flower color as flowers of plants of 'Sunparamiho' were white in color.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparaswepi' grown in a container.

The photograph at the bottom of the sheet is a close-up view of typical flowers of 'Sunparaswepi'.

DETAILED BOTANICAL DESCRIPTION

The aforementioned photographs and following observations, measurements and values describe plants grown during the early autumn in 15-cm containers in an outdoor nursery in Higashiomi, Shiga, Japan and under commercial practice. During the production of the plants, day temperatures averaged 25° C. and night temperatures averaged 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Sunparaswepi'.

Parentage:

*Female, or seed, parent.*—Proprietary selection of *Mandevilla hybrida* identified as code number M-7, not patented.

*Male, or pollen, parent.*—Proprietary selection of *Mandevilla hybrida* identified as code number MW-13, not patented.

Propagation:

*Type.*—By vegetative cuttings.

*Time to initiate roots.*—About two weeks at 23° C. to 25° C.

*Time to produce a rooted young plant.*—About five to six weeks at 23° C. to 25° C.

*Root description.*—Fibrous; light brown in color.

*Rooting habit.*—Freely branching; medium density.

Plant description:

*Plant and growth habit.*—Compact and vining plant habit; vigorous growth habit; freely branching habit.

*Lateral branch description.*—Length: About 174 cm. Diameter: About 3.2 mm. Internode length: About 3.1 cm. Strength: Strong. Texture: Smooth, glabrous. Color, developing: Close to 144A. Color, mature: Close to N199A to N199B.

Foliage description:

*Arrangement.*—Opposite, simple.

*Length.*—About 7 cm.

*Width.*—About 4.3 cm.

*Shape.*—Elliptical.

*Apex.*—Cuspidate.

*Base.*—Obtuse.

*Margin.*—Entire.

*Texture, upper and lower surfaces.*—Smooth, glabrous; leathery.

*Venation pattern.*—Pinnate, reticulate.

*Color.*—Developing leaves, upper surface: Close to 146A. Developing leaves, lower surface: Close to 146C. Fully expanded leaves, upper surface: Close to 137A; venation, close to 145A. Fully expanded leaves, lower surface: Close to 148B; venation, close to 145B.

*Petiole length.*—About 2.3 cm.

*Petiole diameter.*—About 1.6 mm.

*Petiole texture, upper and lower surfaces.*—Smooth, glabrous.

*Petiole color, upper and lower surfaces.*—Close to 143C.

Flower description:

*Flower type and habit.*—Single salverform flowers arranged in axillary racemes; flowers face upright and outwardly; freely flowering habit with about four to five flowers per inflorescence.

*Natural flowering season.*—Plants begin flowering about six weeks after planting; long flowering period, plants flower continuously from early summer to late autumn in Japan.

*Flower longevity on the plant.*—About seven to ten days; flowers not persistent.

*Fragrance.*—None detected.

*Flowers.*—Appearance: Flared trumpet, corolla fused and five-parted; flowers roughly star-shaped. Diameter: About 6.7 cm. Depth (length): About 6.5 cm. Throat diameter: About 1.8 cm. Tube length: About 5.5 cm. Tube diameter, mid-section: About 1.3 cm. Tube diameter, base: About 3.4 mm.

*Flower buds.*—Height: About 7.2 cm. Diameter: About 1.3 cm. Shape: Lenticular. Color: Towards the apex, close to 63D; mid-section, close to 8D; towards the base, close to 145B.

*Corolla.*—Quantity and arrangement: Five petals arranged in a single whorl and fused at the base. Petal length: About 2.8 cm. Petal width: About 2.5 cm. Petal shape: Obovate. Petal apex: Obtuse. Petal margin: Entire; slightly undulate. Petal texture, upper and lower surfaces: Smooth, glabrous; satiny. Throat texture: Smooth, glabrous. Tube texture: Smooth, glabrous. Color: Petal, when opening, upper surface: Close to 68B to 68C. Petal, when opening, lower surface: Close to 62C to 62D and 68D. Petal, fully opened, upper surface: Close to 155D. Petal, fully opened, lower surface: Close to 76D. Throat: Towards the base, close to 17A; mid-section, close to 17C; towards the petal lobes, close to 60D. Tube: Close to 19D.

*Corona.*—Quantity and arrangement: Five sepals arranged in a single whorl. Sepal length: About 7.2 mm. Sepal width: About 2.7 mm. Sepal shape: Trullate. Sepal apex: Acuminate. Sepal base: Obtuse. Sepal margin: Entire. Sepal texture, upper and lower surfaces: Smooth, glabrous. Sepal color: Immature and mature, upper surface: Close to 145A; towards the apex, close to 145B tinted with close to 180C. Immature and mature, lower surface: Close to 145C.

*Peduncles.*—Length: About 2.9 cm. Diameter: About 1.7 mm. Texture: Smooth, glabrous. Strength: Flexible, but strong. Color: Close to 144A.

*Pedicels.*—Length: About 2 cm. Diameter: About 2.2 mm. Texture: Smooth, glabrous. Strength: Flexible, but strong. Color: Close to 145A.

*Reproductive organs.*—Stamens: Quantity and arrangement: Typically five; filaments fused to corolla; anthers, connivent. Anther shape: Ellipsoidal. Anther size: About 1.3 mm by 9.5 mm. Anther color: Close to 10B. Pollen amount: Moderate. Pollen color: Close to 12C. Pistils: Quantity: Typically one. Pistil length: About 2.5 cm. Style color: Close to 8D. Stigma shape: Conical. Stigma color: Close to 8B. Ovary color: Close to 149B.

*Seeds and fruits.*—Seed and fruit production have not been observed on plants of the new *Mandevilla.*

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparaswepi' as illustrated and described.

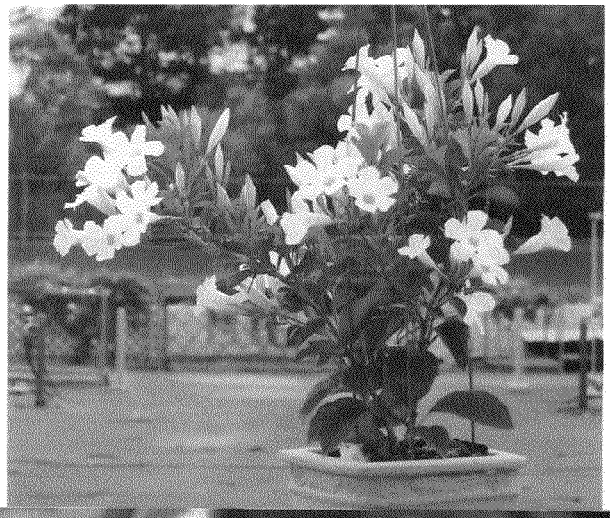
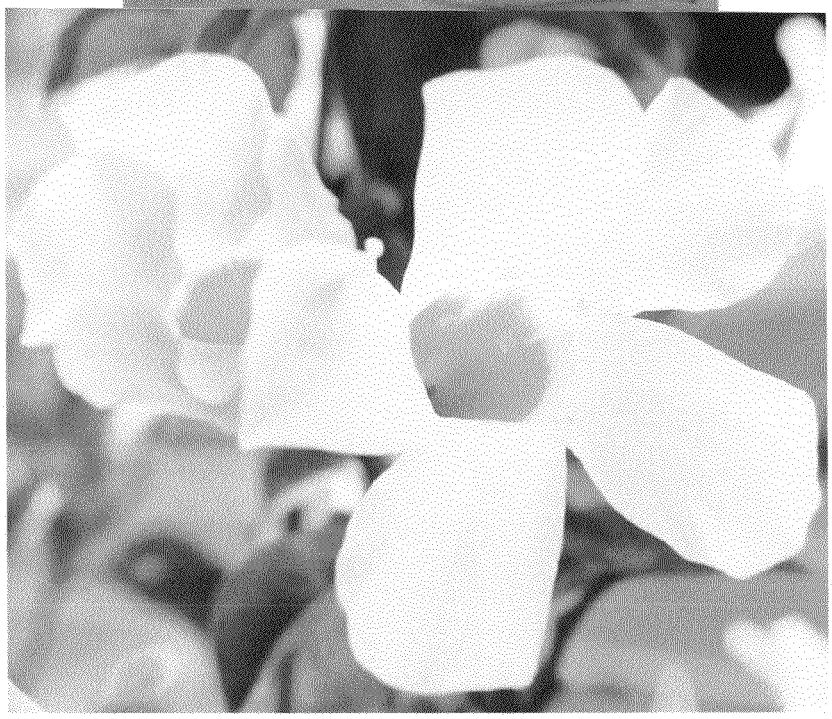

* * * * *